(12) United States Patent
Lewis et al.

(10) Patent No.: US 9,732,142 B2
(45) Date of Patent: *Aug. 15, 2017

(54) INTRACELLULAR ANTIBODY DELIVERY

(75) Inventors: Andrew Lennard Lewis, Farnham (GB); Giuseppe Battaglia, Sheffield (GB); Marzia Massignani, Sheffield (GB)

(73) Assignee: BIOCOMPATIBLES UK LIMITED, Farnham Surrey (GB)

( * ) Notice: Subject to any disclaimer, the term of this patent is extended or adjusted under 35 U.S.C. 154(b) by 762 days.

This patent is subject to a terminal disclaimer.

(21) Appl. No.: 12/991,330

(22) PCT Filed: May 14, 2009

(86) PCT No.: PCT/EP2009/055867
§ 371 (c)(1),
(2), (4) Date: Jan. 24, 2011

(87) PCT Pub. No.: WO2009/138473
PCT Pub. Date: Nov. 19, 2009

(65) Prior Publication Data
US 2011/0111036 A1 May 12, 2011

(30) Foreign Application Priority Data

May 15, 2008 (EP) .................................... 08156270

(51) Int. Cl.
| | | |
|---|---|---|
| C07K 16/00 | (2006.01) | |
| A61K 9/127 | (2006.01) | |
| C08F 290/00 | (2006.01) | |
| C08F 293/00 | (2006.01) | |
| C08L 53/00 | (2006.01) | |
| A61K 39/00 | (2006.01) | |

(52) U.S. Cl.
CPC ............ *C07K 16/00* (2013.01); *A61K 9/1273* (2013.01); *C08F 290/00* (2013.01); *C08F 293/005* (2013.01); *C08L 53/00* (2013.01); *A61K 2039/505* (2013.01)

(58) Field of Classification Search
None
See application file for complete search history.

(56) References Cited

U.S. PATENT DOCUMENTS

| 6,852,816 | B2 * | 2/2005 | Lewis et al. ................. 526/277 |
|---|---|---|---|
| 2005/0163743 | A1 * | 7/2005 | Lewis et al. ................. 424/78.3 |
| 2008/0095847 | A1 * | 4/2008 | Glauser et al. ................ 424/484 |
| 2011/0111036 | A1 * | 5/2011 | Lewis et al. ................. 424/489 |
| 2011/0150941 | A1 * | 6/2011 | Battaglia ....................... 424/400 |
| 2011/0151013 | A1 * | 6/2011 | Lewis et al. ................. 424/497 |

FOREIGN PATENT DOCUMENTS

| WO | 03/074090 A2 | 9/2003 | |
|---|---|---|---|
| WO | WO03/074090 | * 9/2003 | ............. A61K 47/48 |
| WO | 2006/088647 A1 | 8/2006 | |
| WO | 2006/113666 A2 | 10/2006 | |

OTHER PUBLICATIONS

Lomas, H et al. Biomimetic pH Sensitive Polymersomes for Efficient DNA Encapsulation and Delivery. Adv. Mater. vol. 19 (2007), pp. 4238-4243.*
Du, J., et al; pH Sensitive Vesicles based on a Biocompatible Zwitterionic Diblock Copolymer. J. Am. Chem. Soc. 127, 17982-17983 (2005).*
Ray et al: "Encapsulation of Anti-ICAM-1 Antibodies Into PLA-Pegmicrospheres: In Vitro and in Vivo Characterization." Arvo Annual Meeting Abstract Search and Program Planner, vol. 2003, 2003, p. Abstract No. 4450, XP002499718.*
Fariyal Ahmed et al., "Biodegradable polymersomes loaded with both paclitaxel and doxorubicin permeate and shrink tumors, inducing apoptosis in proportion to accumulated drug", Journal of Controlled Release, 2006, pp. 150-158, vol. 116.
Aravind Asokan et al., "Cytosolic delivery of macromolecules 4. Head group-dependent membrane permeabilization by pH-sensitive detergents", Journal of Controlled Release, 2005, pp. 146-153, vol. 106.
F. Checot et al., "pH-responsive micelles and vesicles nanocapsules based on polypeptide diblock copolymers", Biomolecular Engineering, 2007, pp. 81-85, vol. 24.
Bohdana M. Discher et al., "Polymersomes: Tough Vesicles Made from Diblock Copolymers", Science, May 14, 1999, pp. 1143-1146, XP-002352413, vol. 284.
Cristiano Giacomelli et al., "Phosphorylcholine-Based pH-Responsive Diblock Copolyer Micelles as Drug Delivery Vehicles: Light Scattering, Electron Microscopy, and Fluorescence Experiments", Biomacromolecules, 2006, pp. 817-828, vol. 7.
Kevin Letchford et al., "A review of the formation and classification of amphiphilic block copolymer nanoparticulate structures: micelles, nanospheres, nanocapsules and polymersomes", European Journal of Pharmaceutics and Biopharmaceutics, 2007, pp. 259-269, vol. 65.
Hannah Lomas et al., "Non-cytotoxic polymer vesicles for rapid and efficient intracellular delivery", The Faraday Discuss., Royal Society of Chemistry, 2008, pp. 143-159, vol. 139.

(Continued)

Primary Examiner — Maury Audet
(74) Attorney, Agent, or Firm — Sughrue Mion, PLLC

(57) ABSTRACT

The present invention concerns a composition comprising vesicles and encapsulated within the vesicles, an antibody, wherein the vesicles comprise an amphiphilic block copolymer having a hydrophilic and a hydrophobic block.

Methods of delivering the above compositions into cells are also described.

20 Claims, 7 Drawing Sheets
(6 of 7 Drawing Sheet(s) Filed in Color)

(56) References Cited

OTHER PUBLICATIONS

S.K. Ray et al., "Encapsulation of Anti-ICAM-1 Antibodies into PLA-PEG Microspheres: In vitro and in vivo Characterization", Invest Ophthalmol Vis Sci., 2003, E-Abstract 4450, vol. 44, XP-002499718.

Olivier Zelphati et al., "Intracellular Delivery of Proteins with a New Lipid-mediated Delivery System", The Journal of Biological Chemistry, 2001, pp. 35103-35110, vol. 276, No. 37, XP-002993231.

U.S. Appl. No. 12/991,349, filed Nov. 5, 2010, Giuseppe Battaglia.
U.S. Appl. No. 12/991,321, filed Nov. 5, 2010, Andrew Lennard Lewis et al.

* cited by examiner (A)      (B)

(A) (B)

INTRACELLULAR ANTIBODY DELIVERY

CROSS REFERENCE TO RELATED APPLICATIONS

This application is a National Stage of International Application No. PCT/EP2009/055867 filed on May 14, 2009, which claims priority from European Patent Application No. 08156270.4, filed on May 15, 2008, the contents of all of which are incorporated herein by reference in their entirety.

FIELD OF THE INVENTION

The invention relates to delivery systems for introducing antibodies into cells.

BACKGROUND OF THE INVENTION

The controlled delivery of antibodies into cells is currently of great commercial and scientific interest. It was once thought that intact antibody molecules (both endogenous and exogenous) were not able to penetrate viable cells. However, there is now much research that indicates otherwise. Mature autoantibodies penetrating living cells are thought to participate in the pathogenesis of diverse autoimmune diseases, through inducing apoptosis of healthy tissues and cells. The antibodies may also contribute to the breakdown of self-tolerance through presentation of self-antigens to the immune system. The penetration of naturally occurring autoantibodies into immature lymphoid cells may have a physiological role in the immune repertoire in healthy individuals. Increasing interest is being paid to the potential immunotherapeutic role of penetrating antibodies as tools to deliver drugs, isotopes or genes into cells (Ruiz-Arguelles, A., et al, Antibody penetration into living cells: pathogenic, preventive and immuno-therapeutic implications, Current Pharm Design, 2003, 9, 1881). A non-toxic delivery system for intracellular delivery of inherently non-penetrating antibodies could therefore be of great utility.

The delivery of antibodies into cells can be a particular problem either where large numbers of cells are to be analysed or where one wants to study adhesive as well as non-adhesive cells. Several approaches to introduce proteins and other components into cells have been published, such as electroporation, scrape loading, or delivery via liposomes.

Some have reported on other approaches, such as the use of a combination of a novel IgG-capturing protein and hemaglutinating virus of Japan envelope (HVJ-E), an inactivated Sendai virus particle, which can deliver a variety of molecules into mammalian cells via membrane-fusing activity (Kondo, Y. et al, Efficient delivery of antibody into living cells using a novel HVJ envelope vector system, J Immunol Methods, 2008, 332, 10). An antibody delivery reagent based upon this approach known as GENOMONE-CAB has been commercialised for this purpose. It claims to overcome the difficulties involved in experiments using conventional lipid-based reagents by which antibodies are introduced into cells by means of endocytosis. Similarly, in another study, a novel method for the delivery of antibodies into cells using the TAT-fused protein was reported (Lee, K. O. et al, Improved intracellular delivery of glucocerebrosidase mediated by the HIV-1 TAT protein transduction domain, Biochem Biophys Res Comms, 2005, 337, 701). This fusion protein consists of two functional domains, the protein transduction domain of HIV-1 TAT and the B domain of staphylococcal protein A (SpA), which has an ability to bind to the IgG. The TAT-SpA fusion protein was mixed with fluorescent-labelled rabbit IgG and added to cells and the internalization of antibody was analyzed using confocal microscopy and flow cytometry in living cells.

A widely reported method of antibody delivery is the use of liposomal systems. A number of relatively inexpensive lipid-based delivery systems are commercially available. For example, LIPODIN-AB™ and AB-DELIVERIN™ are antibody delivery systems that claim to deliver functional antibodies to their targets; be highly efficient in many cell lines and primary cells; be serum compatible; be suitable for all antibodies; biodegradable whilst retaining high cell viability; and are ready and easy to use. These systems are lipid-based formulations that form non-covalent complexes with antibodies through electrostatic and hydrophobic interactions. It is well-known however, that despite the claims of high cell viability, these cationic lipid and polymer-based systems are notoriously cytotoxic to cells. This would certainly be a more serious problem for any therapeutic treatment for which it is necessary to continually administer the antibody complex over a prolonged period of time.

Walter et al in Eur J Cell Biol, 1986 April; 4(2): 195-202 describe liposome-mediated delivery of antibody to a Drosophila cell line. Antibody was encapsulated together with a dye into liposomes and uptake by cells observed using light microscopy.

Lipid-based systems that rely upon endocytosis to enter the cell also encounter problems associated with inefficient release (escape) from the endosome. In 2006 Carafa M. et al. (*Eur J Pharm Sci*. 2006, 28, 385) presented work regarding pH sensitive vesicles that were able to escape the endosome due to a change in pH. Other work has been done in order to attempt to enhance the cytosolic delivery, for example using tertiary amine-based detergents (Asokan A, Cho M J., *J Control Release*. 2005, 106, 146). However this method affects the viability of cells by partially disrupting the membrane. Other trials were performed using pore-forming agents such as toxin streptolysin O (SLO) which can be used to reversibly permeabilise adherent or nonadherent cells (Walev I, et al, *Proc Natl Acad Sci USA*. 2001, 98, 3185). All of these methods stress the cell and may alter cellular responses giving unreliable results.

An alternative delivery system composed of a trifluoroacetylated lipopolyamine is described in Zelphati et al; Journal of Biological Chemistry; Vol. 276, No. 37, Sep. 14 2001; pp 35103-35110. This cationic lipid formulation is used to enable recombinant proteins, peptides and antibodies to enter viable cells.

A very efficient, non-toxic and non-inflammatory polymer vector for the delivery of DNA within human cells is described in Lomas, H et al. Biomimetic pH Sensitive Polymersomes for Efficient DNA Encapsulation and Delivery. *Adv. Mater*. Vol 19 (2007), pages 4238-4243. In addition, a combination of amphiphilic polymer with DNA is described in WO03/074090. Depending on the block lengths of the respective components of the copolymer, the interaction with DNA can be tailored to produce DNA condensates (polyplexes) or to encapsulate the DNA within a vesicle. The latter is based on the self-assembly of pH sensitive poly (2-methacryloxyethyl phosphorylcholine)-poly (2-(diisopropylamino)-ethyl methacrylate), (PMPC-PDPA) block copolymers into nanometer-sized vesicles, also known as polymersomes (Du, J., et al; pH Sensitive Vesicles based on a Biocompatible Zwitterionic Diblock Copolymer. *J. Am. Chem. Soc*. 127, 17982-17983 (2005)). The use of these polymer vesicles for delivering nucleic acids and rhodamine dyes is further described in Lomas et al; Faraday Discuss.

2008, 139, 143-159. None of these prior art references describe the delivery of antibodies into cells.

SUMMARY OF THE INVENTION

In view of the prior art there remains a desire to provide improved delivery systems for introducing antibodies into cells. In accordance with this desire there is provided in a first aspect of this invention a composition comprising vesicles and encapsulated within the vesicles, an antibody, wherein the vesicles comprise an amphiphilic block copolymer having a hydrophilic and a hydrophobic block.

The second aspect of this invention provides a method for forming a composition according to the first aspect of the invention, wherein one of the blocks is pH-sensitive, comprising the steps:

(i) dispersing the amphiphilic copolymer in an aqueous medium;
(ii) acidifying the composition formed in step (i);
(iii) adding the antibody to the acidified composition; and
(iv) raising the pH to around neutral to encapsulate the antibody.

The third aspect of this invention provides an in vitro method of delivering an antibody into a cell comprising contacting a composition according to the first aspect of the invention with the cell.

The fourth aspect of the invention provides a composition according to the first aspect of the invention for use in a method of treatment by therapy.

The final aspect of the invention provides a composition according to the first aspect of the invention for use in a method of treatment by therapy, wherein an antibody is delivered into a cell.

The vesicles defined in the first aspect of the invention are biocompatible and do not undergo any cytotoxic interactions with cells. The vesicle-forming polymer is well accepted by the cell and induces no inflammatory response, and can be used to deliver antibodies to cells without undue toxicity. Delivery rates are improved compared to the delivery systems described in the prior art.

Due to the inability of most antibodies to naturally enter cells, past experiments using antibodies have focused primarily on extracellular binding. Since the present invention allows target molecules to enter into living cells, it is now possible to pursue new dimensions of research, for instance, exploration of target molecules for disease diagnosis and treatment. The present invention provides a novel method for introducing antibodies which retain and carry out their function within cells, and is useful for a number of purposes, including the study of intracellular events relating to targeted molecules in living cells. Many questions concerning the function of the cytoskeleton can be addressed using functional antibodies either by in vitro assay or in whole cell systems. Ultimately, the function of a component has to be studied within intact cell systems and the present invention allows such systems to be used.

The invention described herein is concerned with the use of block copolymers that form vesicles, otherwise known as "polymersomes" for the encapsulation of antibodies or antibody fragments, and for the subsequent delivery of the antibody into a live cell without inducing toxicity within that cell. The use of polymersomes in intracellular delivery has been previously described, as detailed above, and there have been wide-ranging reports of the functionalisation of the polymersome surfaces with antibodies to aid in the targeting of these vesicles to particular cells. We are not aware however, of the reported use of these structures for the encapsulation of antibodies and use to deliver, directly into live cells, intact antibody with the capability of binding to internal target structures for altering cell function for therapeutic or diagnostic use. Therefore according to the invention, the antibody is one which can bind internal target structures.

In this invention self-assembled structures comprising amphiphilic block copolymers are used. These are able to mimic biological phospholipids. Molecular weights of these polymers are much higher than naturally-occurring phospholipid-based surfactants such that they can assemble into more entangled membranes, (Battaglia, G. & Ryan, A. J. J. Am. Chem. Soc. 2005, 127, 8757) providing a final structure with improved mechanical properties and colloidal stability. Furthermore, the flexible nature of the copolymer synthesis allows the application of different compositions and functionalities over a wide range of molecular weights and consequently of membrane thicknesses. Thus the use of these block copolymers as delivery vehicles offers significant advantages over those vehicles used in the prior art.

DETAILED DESCRIPTION OF THE INVENTION

Once the vesicles are taken up into cells, they advantageously dissociate and release the antibody within the cell. Dissociation may be promoted by a variety of mechanisms, but is typically promoted by pH sensitivity of the block copolymer. It is preferred that the hydrophilic or the hydrophobic block of the amphiphilic copolymer, preferably the hydrophobic block, has a pendant group with a $pK_a$ in the range 3.0 to 6.9. Without wishing to be bound by theory, the mechanism of cell internalisation (endocytosis) of the vesicles involves engulfment within phospholipid membranes produced by endocytic organelles such as trafficking vesicles, phagosomes, or pinosomes (depending on the precise endocytic pathway). The endocytic organelle detaches from the cell membrane and takes the vesicles inside the cell for further processing. Regardless of the endocytic pathway, the internalised vesicles experience a reduction in local pH from pH 7.4 to pH 5-6 once inside the organelle. This pH drop is sufficient to trigger disintegration of the vesicles and release of the antibody. As this transition is confined within a semi-permeable organelle membrane, the sudden increase in particle number corresponds to a large increase in osmotic pressure. This causes lysis of the phospholipid membrane of the endocytic organelle, releasing the antibody into the cell cytosol.

The composition of this invention is normally aqueous and typically therefore the vesicles are in aqueous solution. A typical pH of the aqueous composition is 7.0 to 7.6, preferably 7.2 to 7.4. Vesicles are generally substantially spherical and comprise a bilayered membrane. The bilayer is generally formed from two layers of amphiphilic molecules, which align to form an enclosed core with hydrophilic head groups facing the core and the exterior of the vesicle, and hydrophilic tail groups forming the interior of the membrane.

A typical diameter of a substantially spherical vesicle is in the range 50-5000 nm. More typically, the diameter is in the range 50-1000 nm. Vesicles having a diameter in this range are normally termed "nanovesicles". The nanovesicles are preferably substantially spherical in shape. Typically, the nanovesicles have a number average diameter of less than 300 nm, preferably less than 250 nm, most preferably less than 200 nm or 150 nm. The thickness of the bilayer is generally between 2 to 50 nm, more typically between 5 and 20 nm. These dimensions can be measured by Transmission Electron Microscopy (T. E. M), and Small Angle X-ray Scattering (SAXS) (Battaglia et al; JACS127, 8757 (2005)).

The antibody which is delivered into the cell may be a primary antibody or a secondary antibody. In one embodiment of this invention, both a primary and a secondary antibody are delivered into the cells, typically in separate populations of vesicles. The secondary antibody may carry a label which makes it useful for imaging, purification or cell-sorting applications. The antibody may be conjugated to an imaging agent such as a fluorescent dye. In a further embodiment, an antibody and an imaging agent are independently associated with the vesicles.

A suitable label for use in the present invention is any label which fluoresces when excited with electromagnetic radiation, and can be associated with the self-assembled structures or the antibody. Typically, the fluorescent label is encapsulated within the aqueous core of the vesicles. However, when the fluorescent label is hydrophobic, more typically it is associated with the hydrophobic membrane. Fluorescent dyes, such as rhodamine fluorescein, BODIPY® and NBD are particularly suitable.

Resolution may be improved by coupling a labelled antibody to a quencher molecule such as trypan blue. A quencher is a molecule able to absorb the emission energy from an excited fluorophore, reducing its fluorescence signal. In order to obtain the quenching effect the donor (fluorophore) and the acceptor (quencher) must be no further then 100 Å apart. Example 8 contains more details of the use of this quenching technique.

Suitable antibodies include those which target intracellular structures including the centrosome, endosomes, the endoplasmic reticulum and Golgi proteins, lysosomes, mitochondrial proteins, the nuclear envelope, peroxisomes, the plasma membrane and other cellular and organelle proteins.

The antibody may be a whole antibody molecule (for instance IgG), or alternatively a fragment of an antibody (such as the single chain antigen-binding site scFvs). Examples of antibodies which may be used in the present invention include:

Tumour therapy antibodies (such as antibodies against tyrosine kinases receptors, for example EGF receptor, erb2 receptor; inhibitors of signal transduction pathways such as Ras; and apoptosis pathway antibodies such as caspases); nuclear factors involved in inducing cell growth arrest and death (e.g. p53), cell cycle proteins (for instance cyclins) and extracellular proteinases involved in tumour progression (for instance metalloproteases and cathepsins).

Antibodies which may treat infectious diseases (for instance HIV virus therapy antibodies and HVC inhibitors).

Antibodies involved in intracellular immune suppression and inflammatory pathways suppression such as the blocking of immune rejection by MCH-I antibody therapy, and the blocking of inflammatory pathways intracellularly (antiNFκB antibodies).

Potential applications and target proteins for antibodies which may find use in the present invention are summarized in the table below:

| Applications | Target |
| --- | --- |
| Antiviral | HIV-glycoprotein 120 |
| | HIV-1 Integrase (IN) |
| | HEPC-NS3 protein |

-continued

| Applications | Target |
| --- | --- |
| Anticancer | Viral oncoprotein E7 (human papillomavirus type 16) |
| | Cyclin E |
| | H-RAS |
| | erB2 |
| | Caspases (e.g. caspase-3) |
| Neurobiology | Alzheimer-Tau protein |
| | Alzheimer-β-amyloid precursor |
| | Bax |
| | PrP prion protein |
| | Hungtingtin |
| Intracellular immune/ inflammation suppression | Suppression of MHC-I |
| | NF$_K$B p65 |
| Stem cell differentiation | Sox9 |
| | Runx |
| | Osterix |
| Cell signalling | p13-kinase |
| | Raf-1 |
| | Ral |
| Nuclear targets | Cell cycle regulation proteins (cyclins) |
| | p53 |
| | Heterochromatin protein 1 |

The antibody is typically associated with the vesicles via physical or chemical interaction, such as electrostatic or hydrophobic attraction. Usually the antibody is not covalently bound to the vesicles. The antibody may be associated with the interior of the membrane. Preferably the antibody is encapsulated within the aqueous core of the vesicle, which is preferably a nanovesicle.

A variety of experimental techniques can be used to determine the association between the antibody and the vesicles. For instance, Transition Electron Microscopy and Dynamic Light Scattering (DLS) can be used to show that the antibody is encapsulated within the core of the vesicles. Zeta-potential measurements may also be used to confirm that the antibody is encapsulated, rather than associated with the outer membrane of the vesicles.

The hydrophobic or the hydrophilic block of the amphiphilic block copolymer preferably comprises pendant groups which have a $pK_a$ in the range 3.0 to 6.9. This confers "pH sensitivity" on the copolymer. By $pK_a$, is meant the pH where half of the pendant groups are ionised. Typically, the hydrophobic block has the pendant groups with a $pK_a$ in the range 3.0 to 6.9.

$pK_a$ can be determined by a variety of methods including pH titration followed by potentiometric titration, UV spectroscopy and Dynamic Light Scattering (DLS). An appropriate method should be selected to measure the $pK_a$ according to the copolymer which is being analysed and its solubility in the test media.

DLS is the particularly preferred method for measuring $pK_a$. As indicated in the paper by Du et al; J. Am. Chem. Soc 2005, 127, 17982-17983, the DLS signal from PMPC$_{25}$-b-PDPA$_{120}$ copolymer in water varies with pH. At a certain pH the signal rapidly increases as the copolymer undergoes a transition from being molecularly deassociated to associated. The $pK_a$ is taken as the pH of the mid-point of this rapid increase. These experiments are described further in Giacomelli et al, Biomacromolecules 2006, 7, 817-828. In this reference, the experiments are performed on micelles of PMPC-b-PDPA block copolymer, but the techniques may also be used when the phase transition involves vesicle formation.

In the specification, the $pK_a$ of a group in a polymer is determined on the basis of a polymer system (and not assumed to be the same as the $pK_a$'s of similar moieties in non-polymeric systems).

It is preferred that the hydrophobic block comprise pendant cationisable moieties as pendant groups. Cationisable moieties are, for instance, primary, secondary or tertiary amines, capable of being protonated at pH's below a value in the range 3 to 6.9. Alternatively the group may be a phosphine.

Preferably, the $pK_a$ of the pendant groups is in the range 4.0 to 6.9, more preferably 5.5 to 6.9. The vesicles are correspondingly capable of disassociating in such pH ranges.

In one embodiment of the invention, the hydrophobic block has a degree of polymerisation of at least 50, more preferably at least 70. Preferably, the degree of polymerisation of the hydrophobic block is no more than 250, even more preferably, no more than 200. Typically, the degree of polymerisation of the hydrophilic block is at least 15, more preferably at least 20. It is preferred that the ratio of the degree of polymerisation of the hydrophilic to hydrophobic block is in the range 1:2.5 to 1:8. All of these limitations promote vesicle, rather than micelle formation.

In the invention, although the hydrophilic block may be based on condensation polymers, such as polyesters, polyamides, polyanhydrides, polyurethanes, polyethers (including polyalkylene glycols, especially PEG), polyimines, polypeptides, polyureas, polyacetals or polysaccharides, preferably the hydrophilic block is based on a radical polymerised addition polymer of ethylenically unsaturated monomers. Generally the monomers from which the block is formed themselves have zwitterionic pendant groups which remain unchanged in the polymerisation process. It may alternatively be possible to derivatise a functional pendant group of a monomer to render it zwitterionic after polymerisation.

Preferably, the hydrophilic block is formed from ethylenically-unsaturated zwitterionic monomers. Suitable ethylenically unsaturated zwitterionic monomers have the general formula $$Y\ B\ X \qquad\qquad I$$

In which Y is an ethylenically unsaturated group selected from $H_2C=CR-CO-A-$, $H_2C=CR-C_6H_4-A^1-$, $H_2C=CR-CH_2A^2$, $R^2O-CO-CR=CR-O$, $RCH=CH-CO-O-$, $RCH=C(COOR^2)CH_2-CO-O$,

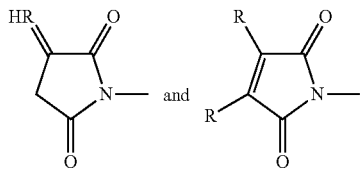

A is $-O-$ or $NR^1$;
$A^1$ is selected from a bond, $(CH_2)_lA^2$ and $(CH_2)_lSO_3^-$ in which I is 1 to 12;
$A^2$ is selected from a bond, $-O-$, $O-CO-$, $CO-O$, $CO-NR^1-$, $-NR^1-CO$, $O-CO-NR^1-$, $NR^1-CO-O-$;
R is hydrogen or $C_{1-4}$ alkyl;
$R^1$ is hydrogen, $C_{1-4}$ alkyl or BX;
$R^2$ is hydrogen or $C_{1-4}$ alkyl;
B is a bond, or a straight branched alkanediyl, alkylene oxaalkylene, or alkylene (oligooxalkylene) group, optionally containing one or more fluorine substituents;
X is a zwitterionic group.

Preferably X is an ammonium, phosphonium, or sulphonium phosphate or phosphonate ester zwitterionic group, more preferably a group of the general formula II

in which the moieties $A^3$ and $A^4$, which are the same or different, are $-O-$, $-S-$, $-NH-$ or a valence bond, preferably $-O-$, and $W^+$ is a group comprising an ammonium, phosphonium or sulphonium cationic group and a group linking the anionic and cationic moieties which is preferably a $C_{1-12}$-alkanediyl group, preferably in which $W^+$ is a group of formula

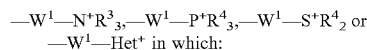

$W^1$ is alkanediyl of 1 or more, preferably 2-6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^3$ are the same or different and each is hydrogen or alkyl of 1 to 4 carbon atoms, preferably methyl, or aryl, such as phenyl, or two of the groups $R^3$ together with the nitrogen atom to which they are attached form an aliphatic heterocyclic ring containing from 5 to 7 atoms, or the three groups $R^3$ together with the nitrogen atom to which they are attached as heteroaromatic ring having 5 to 7 atoms, either of which rings may be fused with another saturated or unsaturated ring to form a fused ring structure containing from 5 to 7 atoms in each ring, and optionally one or more of the groups $R^3$ is substituted by a hydrophilic functional group, and the groups $R^4$ are the same or different and each is $R^3$ or a group $OR^3$, where $R^3$ is as defined above; or Het is an aromatic nitrogen-, phosphorus- or sulphur-, preferably nitrogen-, containing ring, for example pyridine.

Monomers in which X is of the general formula in which $W^+$ is $W^1N^+R^3_3$ may be made as described in our earlier specification WO-A-9301221. Phosphonium and sulphonium analogues are described in WO-A-9520407 and WO-A-9416749.

Generally a group of the formula II has the preferred general formula III

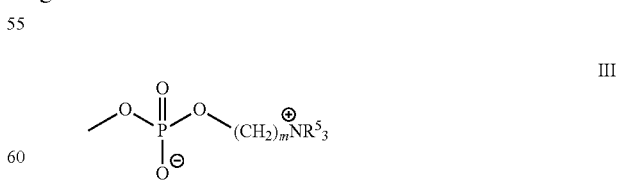

where the groups $R^5$ are the same or different and each is hydrogen or $C_{1-4}$ alkyl, and m is from 1 to 4, in which preferably the groups $R^5$ are the same preferably methyl.

In phosphobetaine based groups, X may have the general formula IV

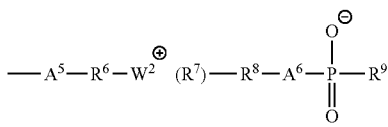

IV in which $A^5$ is a valence bond, —O—, —S— or —NH—, preferably —O—;

$R^6$ is a valence bond (together with $A^5$) or alkanediyl, —C(O)alkylene- or —C(O)NH alkylene preferably alkanediyl, and preferably containing from 1 to 6 carbon atoms in the alkanediyl chain;

$W^2$ is S, $PR^7$ or $NR^7$;

the or each group $R^7$ is hydrogen or alkyl of 1 to 4 carbon atoms or the two groups $R^7$ together with the heteroatom to which they are attached form a heterocyclic ring of 5 to 7 atoms;

$R^8$ is alkanediyl of 1 to 20, preferably 1 to 10, more preferably 1 to 6 carbon atoms;

$A^6$ is a bond, NH, S or O, preferably O; and $R^9$ is a hydroxyl, $C_{1-12}$ alkyl, $C_{1-12}$ alkoxy, $C_{7-18}$ aralkyl, $C_{7-18}$-aralkoxy, $C_{6-18}$ aryl or $C_{6-18}$ aryloxy group.

Monomers comprising a group of the general formula IV may be made by methods as described in JP-B-03-031718, in which an amino substituted monomer is reacted with a phospholane.

In compounds comprising a group of the general formula IV, it is preferred that $A^5$ is a bond;

$R^6$ is a $C_{2-6}$ alkanediyl;

$W^2$ is $NR^7$:

each $R^7$ is $C_{1-4}$ alkyl;

$R^8$ is $C_{2-6}$ alkanediyl;

$A^6$ is O; and $R^9$ is $C_{1-4}$ alkoxy.

Alternatively X may be a zwitterion in which the anion comprises a sulphate, sulphonate or carboxylate group.

One example of such a group is a sulphobetaine group, of the general formula V

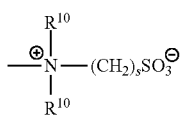

V where the groups $R^{10}$ are the same or different and each is hydrogen or $C_{1-4}$ alkyl and s is from 2 to 4.

Preferably the groups $R^{10}$ are the same. It is also preferable that at least one of the groups $R^{10}$ is methyl, and more preferable that the groups $R^{36}$ are both methyl.

Preferably s is 2 or 3, more preferably 3.

Another example of a zwitterionic group having a carboxylate group is an amino acid moiety in which the alpha carbon atom (to which an amine group and the carboxylic acid group are attached) is joined through a linker group to the backbone of the biocompatible polymer. Such groups may be represented by the general formula VI

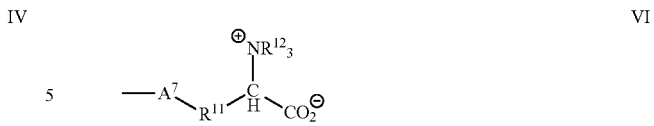

VI in which $A^7$ is a valence bond, —O—, —S— or —NH—, preferably —O—, $R^{11}$ is a valence bond (optionally together with $A^7$) or alkanediyl, —C(O)alkylene- or —C(O)NHalkylene, preferably alkanediyl and preferably containing from 1 to 6 carbon atoms; and the groups $R^{12}$ are the same or different and each is hydrogen or alkyl of 1 to 4 carbon atoms, preferably methyl, or two or three of the groups $R^{12}$, together with the nitrogen to which they are attached, form a heterocyclic ring of from 5 to 7 atoms, or the three group $R^{12}$ together with the nitrogen atom to which they are attached form a fused ring heterocyclic structure containing from 5 to 7 atoms in each ring.

Another example of a zwitterion having a carboxylate group is a carboxy betaine —$N^+$ $(R^{13})_2(CH_2)_rCOO^-$ in which the $R^{13}$ groups are the same or different and each is hydrogen or $R_{1-4}$ alkyl and r is 2 to 6, preferably 2 or 3.

In the zwitterionic monomer of the general formula I it is preferred that the ethylenic unsaturated group Y is $H_2C$=CR—CO-A-. Such acrylic moieties are preferably methacrylic, that is in which R is methyl, or acrylic, in which R is hydrogen. Whilst the compounds may be (meth)acrylamido compounds (in which A is $NR^1$), in which case $R^1$ is preferably hydrogen, or less preferably, methyl, most preferably the compounds are esters, that is in which A is O.

In monomers of the general formula I, especially where Y is the preferred (alk)acrylic group, B is most preferably an alkanediyl group. Whilst some of the hydrogen atoms of such group may be substituted by fluorine atoms, preferably B is an unsubstituted alkanediyl group, most preferably a straight chain group having 2 to 6 carbon atoms.

A particularly preferred zwitterionic monomer is 2-methacryloyloxyethyl-phosphorylcholine (MPC). Mixtures of zwitterionic monomers each having the above general formula may be used.

The hydrophobic block may be formed of condensation polymers, such as polyethers (including polyalkylene glycols), polyesters, polyamides, polyanhydrides, polyurethanes, polyimines, polypeptides, polyureas, polyacetals, or polysiloxanes. One example of a suitable hydrophobic block is polyalkylene oxide, usually polypropylene oxide, that is the same type of block as has been used in the well-studied Pluronic/Poloxamer based systems. One type of highly hydrophobic block is poly(dimethylsiloxane). In one preferred embodiment the type of polymer forming the hydrophobic block is the same as that forming the hydrophilic block. Preferably the polymer is formed by radical polymerisation of ethylenically unsaturated monomers.

Suitable monomers from which the hydrophobic block may be formed have the general formula VII $Y^1B^1Q$          VII in which $Y^1$ is selected from $H_2C$=$CR^{14}$—CO-$A^8$-, $H_2C$=$CR^{14}$—$C_6H_4$-$A^9$-, $H_2C$=$CR^{14}$—$CH_2A^{10}$, $R^{16}O$—CO—$CR^{14}$=$CR^{14}$—CO—O, $R^{14}CH$=CH—CO—O—, $R^{14}CH$=C(COO$R^{16}$)$CH_2$—CO—O,

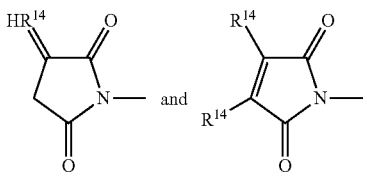

$A^8$ is —O— or $NR^{15}$;

$A^9$ is selected from a bond, $(CH_2)_q A^{10}$ and $(CH_2)_q SO_3^-$ in which q is 1 to 12;

$A^{10}$ is selected from a bond, —O—, O—CO—, CO—O—, CO—$NR^{15}$—, —$NR^{15}$—CO—, O—CO—$NR^{15}$—, $NR^{15}$—CO—O—;

$R^{14}$ is hydrogen or $C_{1-4}$ alkyl;

$R^{15}$ is hydrogen, $C_{1-4}$ alkyl or $B^1$ Q;

$R^{16}$ is hydrogen or $C_{1-4}$ alkyl;

$B^1$ is a bond, or a straight branched alkanediyl, alkylene oxaalkylene, or alkylene (oligooxalkylene) group, optionally containing one or more fluorine substituents; and Q is a cationic or cationisable group of the formula —$NR^{17}_p$, —$PR^{17}_p$ and $SR^{17}_r$, in which p is 2 or 3, r is 1 or 2, the groups $R^{43}$ are the same or different and each is selected from the group consisting of hydrogen, $C_{1-24}$ alkyl and aryl, or two of the groups $R^{17}$ together with the heteroatom to which they are attached from a 5 to 7 membered heterocyclic ring or three $R^{17}$ groups together with the heteroatom to which they are attached form a 5 to 7 membered heteroaromatic ring, either of which rings may be fused to another 5 to 7 membered saturated or unsaturated ring, and any of the $R^{43}$ groups may be substituted by amino or hydroxyl groups or halogen atoms; wherein if p is 3, at least one of the groups $R^{17}$ is hydrogen.

Preferably $Y^1$ is $H_2C=CR^{14}$—CO-$A^8$-where $R^{14}$ is H or methyl and $A^8$ is O or NH.

Preferred groups $B^1$ are alkanediyl, usually with linear alkyl chains and preferably having 2 to 12 carbon atoms, such as 2 or 3 carbon atoms.

Preferably Q is $NR^{17}_2$ where $R^{17}$ is $C_{1-12}$-alkyl. Preferably both $R^{17}$'s are the same. Particularly useful results have been achieved where the groups $R^{17}$ are $C_{1-4}$ alkyl, especially ethyl, methyl or isopropyl.

Either or both the hydrophobic and hydrophilic blocks may include comonomers, for instance to provide functionality, control over hydrophobicity, control over pH sensitivity, $pK_a$ or $pK_b$ as the case may be, control over temperature sensitivity or as general diluents. For instance comonomers providing functionality may be useful to provide conjugation of pendant groups following polymerisation and/or vesicle formation, to targeting moieties, or to provide for conjugation between the biologically active molecule and the polymer. Alternatively, functional groups may allow for crosslinking of the polymer following vesicle formation, to confer increased stability on the vesicle structure.

Examples of suitable comonomers are compounds of the general formula VIII

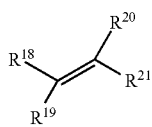

VIII in which $R^{18}$ is selected from hydrogen, halogen, $C_{1-4}$ alkyl and groups $COOR^{22}$ in which $R^{22}$ is hydrogen and $C_{1-4}$ alkyl;

$R^{19}$ is selected from hydrogen, halogen and $C_{1-4}$ alkyl;

$R^{20}$ is selected from hydrogen, halogen, $C_{1-4}$ alkyl and groups $COOR^{22}$ provided that $R^{18}$ and $R^{20}$ are not both $COOR^{22}$; and $R^{21}$ is a $C_{1-10}$ alkyl, a $C_{1-20}$ alkoxycarbonyl, a mono- or di-($C_{1-20}$ alkyl) amino carbonyl, a $C_{6-20}$ aryl (including alkaryl) a $C_{7-20}$ aralkyl, a $C_{6-20}$ aryloxycarbonyl, a $C_{1-20}$-aralkyloxycarbonyl, a $C_{6-20}$ arylamino carbonyl, a $C_{7-20}$ aralkyl-amino, a hydroxyl or a $C_{2-10}$ acyloxy group, any of which may have one or more substituents selected from halogen atoms, alkoxy, oligo-alkoxy, aryloxy, acyloxy, acylamino, amine (including mono and di-alkyl amino and trialkylammonium in which the alkyl groups may be substituted), carboxyl, sulphonyl, phosphoryl, phosphino, (including mono- and di-alkyl phosphine and tri-alkylphosphonium), zwitterionic, hydroxyl groups, vinyloxycarbonyl and other vinylic or allylic substituents, and reactive silyl or silyloxy groups, such as trialkoxysilyl groups;

or $R^{21}$ and $R^{20}$ or $R^{21}$ and $R^{19}$ may together form —$CONR^{23}CO$ in which $R^{23}$ is a $C_{1-20}$ alkyl group.

It is preferred for at least two of the groups $R^{18}$, $R^{19}$, $R^{20}$ and $R^{21}$ to be halogen or, more preferably, hydrogen atoms. Preferably $R^{18}$ and $R^{19}$ are both hydrogen atoms. It is particularly preferred that compound of general formula X be a styrene-based or acrylic based compound. In styrene based compounds $R^{21}$ represents an aryl group, especially a substituted aryl group in which the substituent is an amino alkyl group, a carboxylate or a sulphonate group. Where the comonomer is an acrylic type compound, $R^{21}$ is an alkoxycarbonyl, an alkyl amino carbonyl, or an aryloxy carbonyl group. Most preferably in such compounds $R^{21}$ is a $C_{1-20}$-alkoxy carbonyl group, optionally having a hydroxy substituent. Acrylic compounds are generally methacrylic in which case $R^{20}$ is methyl.

Preferably the comonomer is a non-ionic comonomer, such as a $C_{1-24}$ alkyl(alk)-acrylate or -acrylamide, mono- or di-hydroxy-$C_{1-6}$-alkyl(alk)-acrylate, or acrylamide, oligo ($C_{2-3}$ alkoxy) $C_{2-18}$-alkyl (alk)-acrylate, or -acrylamide, styrene, vinylacetate or N-vinyllactam.

For optimum nanovesicle formation, the block copolymers should have controlled molecular weights. It is preferable for each of the blocks to have molecular weight controlled within a narrow band, that is, to have a narrow polydispersity. The polydispersity of molecular weight should, for instance, be less than 2.0, more preferably less than 1.5, for instance in the range 1.1 to 1.4.

Of course, in the preferred embodiment of this invention wherein one of the blocks has a $pK_a$ in the range 3.0 to 6.9, the blocks should be selected so that they have the requisite $pK_a$ value.

In one embodiment of this invention, the monomer from which the hydrophobic block is formed is 2-(diisopropylamino)ethyl methacrylate (DPA) or 2-(diethylamino)ethyl methacrylate (DEA). In another embodiment, the hydrophilic block is PMPC. Preferably, the copolymer is a PMPC-b-PDPA block copolymer.

Preferably, the block copolymer has general formula $PMPC_m$-b-$PDPA_n$, wherein m is in the range 15-30 (for instance, 25) and n is 50 to 180 or 70 to 180, preferably 100 to 160, more preferably 120 to 160.

Typically, the hydrophobic block is not formed from 2-(dimethyl)ethyl methacrylate (DMA) monomers.

The block copolymer may be a simple A-B block copolymer, or may be an A-B-A or B-A-B block copolymer (where A is the hydrophilic block and B is the hydrophobic block). It may also be an A-B-C, A-C-B or B-A-C block copolymer, where C is a different type of block. C blocks may, for instance, comprise functional, e.g. cross-linking or ionic groups, to allow for reactions of the copolymer, for instance in the novel compositions. Crosslinking reactions especially of A-C-B type copolymers, may confer useful stability on nanovesicles. Cross-linking may be covalent, or sometimes, electrostatic in nature. Cross-linking may involve addition of a separate reagent to link functional groups, such as using a difunctional alkylating agent to link two amino groups. The block copolymer may alternatively be a star type molecule with hydrophilic or hydrophobic core, or may be a comb polymer having a hydrophilic backbone (block) and hydrophobic pendant blocks or vice versa. Such polymers may be formed for instance by the random copolymerisation of monounsaturated macromers and monomers.

The details of the process for polymerising the monomers which are used in this invention are to be found in WO 03/074090.

The living radical polymerisation process has been found to provide polymers of zwitterionic monomers having a polydispersity (of molecular weight) of less than 1.5, as judged by gel permeation chromatography. Polydispersities in the range 1.2 to 1.4 for the or each block are preferred.

An advantage of the present invention where the hydrophobic block is pH sensitive, is that the vesicles may be loaded using a pH change system. In such a process, polymer is dispersed in aqueous liquid in ionised form, in which it solubilises at relatively high concentrations without forming vesicles. Subsequently the pH is changed such that some or all of the ionised groups become deprotonated so that they are in non-ionic form. At the second pH, the hydrophobicity of the block increases and vesicles are formed spontaneously.

The method of forming vesicles with antibody encapsulated in the core wherein one of the blocks is pH-sensitive, may involve the following steps:
 (i) dispersing the amphiphilic copolymer in an aqueous medium;
 (ii) acidifying the composition formed in step (i);
 (iii) adding the antibody to the acidified composition; and
 (iv) raising the pH to around neutral to encapsulate the antibody.

This method preferably comprises a preliminary step wherein the amphiphilic copolymer is dispersed in an organic solvent in a reaction vessel and the solvent is then evaporated to form a film on the inside of the reaction vessel.

By "pH-sensitive", is meant that one of the blocks has a group which becomes protonated/deprotonated at a particular pH. Preferably, one of the blocks, and typically the hydrophobic block comprises pendant groups which have a pKa in the range 3.0 to 6.9, for instance, 4.0 to 6.9. Step (ii), of acidifying the composition, typically reduces the pH to a value below the pKa of the pendant group.

In more detail, vesicles are typically prepared by dissolving copolymer in an organic solvent, such as a 2:1 chloroform:methanol mix in a glass container. Solvent can be evaporated under vacuum leaving a copolymeric film deposited on the walls of the container. The film is then re-hydrated with an aqueous solution, for instance using phosphate buffer saline. The pH of the resultant suspension is decreased to a pH of around 2, to solubilise the film, and then increased slowly to a pH or around 6. Once the pH has reached this value, antibody is typically added. The pH is then increased to around neutral, to encapsulate the antibody. The dispersion may then be sonicated and extruded, for instance using a bench top extruder. UV spectroscopy may be used to calculate the encapsulation efficiency, using techniques well known in the art.

An alternative method for forming vesicles with encapsulated antibody may involve simple equilibration of the antibody and polymer vesicles in water. For instance antibody may be contacted in solid form with an aqueous dispersion of polymer vesicles and incubated, optionally with shaking, to solubilise the active in the dispersed vesicles. Alternatively, antibody dissolved in organic solvent may be emulsified into an aqueous dispersion of polymer vesicles, whereby solvent and antibody become incorporated into the core of the vesicles, followed by evaporation of solvent from the system.

The vesicles used in the invention may be formed from two or more different block copolymers. For instance, they may be formed from a block copolymer comprising a polyalkylene oxide hydrophilic block, and from a block copolymer which has a hydrophilic block comprising a zwitterionic monomer. In this embodiment, in the method of forming vesicles, a mixture of the two block copolymers is used. A suitable mixture would be, for instance, a 75:25 ratio by weight of PMPC-PDPA and PEO-PDPA.

Generally, 0.01% to 10% (w/w) of antibody is mixed with copolymer in the methods described above.

The vesicles associated with antibodies are contacted with cells in a manner such as to promote uptake of the vesicles by the cells. Typically, the cells are grown in culture medium and then seeded on a suitable support such as a well plate or a coverslip. The vesicles are then added directly to the cells on the support. Typically, a known volume of aqueous dispersion of vesicles (for instance, 5-20 mg/ml in PBS) is added to the cells in their culture media.

The cells which are contacted with the antibody-loaded vesicles may be human or animal cells, including primary cells, cancer cells and stem cells.

The application file contains at least one drawing executed in color. Copies of this patent or patent application publication with color drawing(s) will be provided by the Office upon request and payment of the necessary fee.

The invention will now be illustrated by the following Examples and Figures, wherein.

Figure 8:
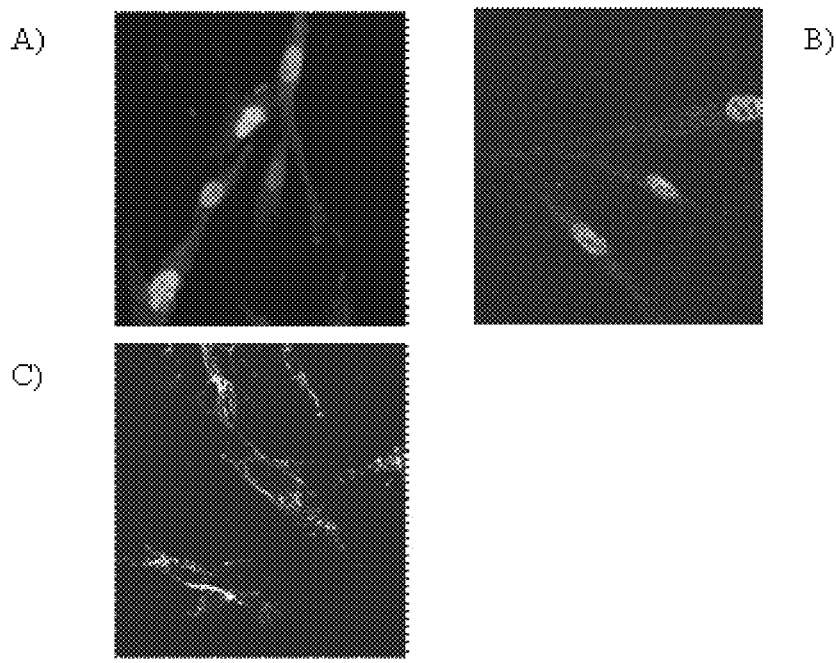
Figure 9:
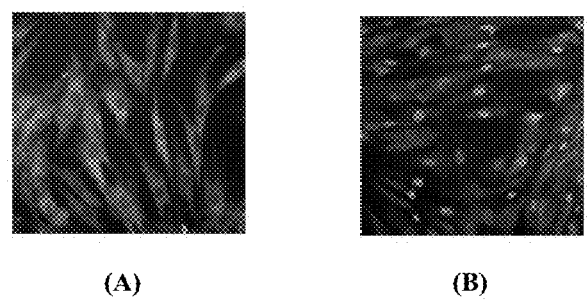
Figure 10:
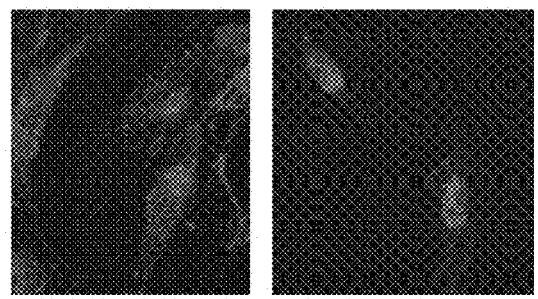
Figure 11:
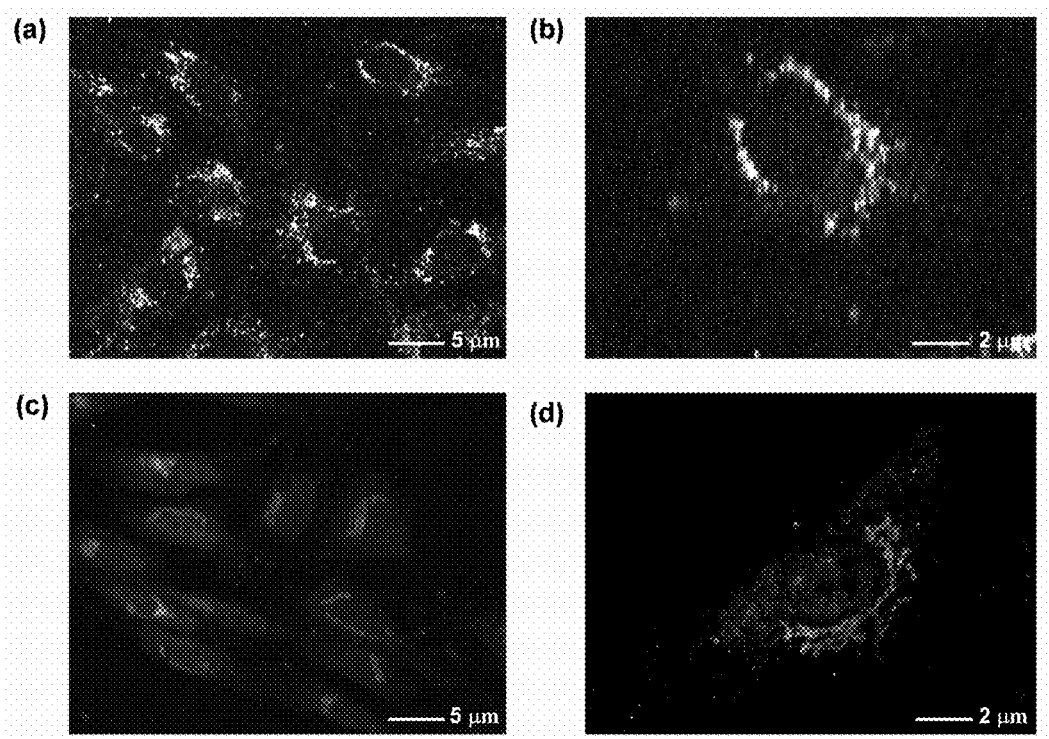
Figure 12:
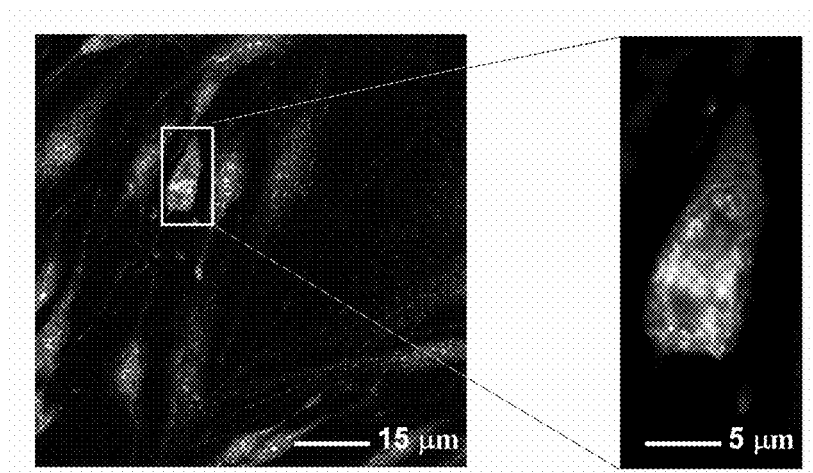

FIG. 8 shows CLSM micrographs of live HDF cells loaded with polymersomes encapsulating FITC labeled anti p65: a) Cells were stimulated (2 h) with 1 μg/mL of LPS 6 h after polymersome-antip65NFκB antibody uptake; b) Cells were stimulated with 1 μg/mL of LPS 2 h prior to polymersome-antip65NFκB antibody uptake; c) Cells were treated with polymersome-antip65NFκB antibody for 6 h uptake (negative control, unstimulated cells);

FIG. 9 shows fluorescence microscopy micrographs showing traditional immunolabeling of NFκB p65 in HDFs—cells were fixed and permeated with triton x-100 prior to antibody treatment: a) Negative control (unstimulated cells); b) Cells were stimulated for 2 h with 1 μg/mL of LPS prior to being fixed;

FIG. 10 shows CLSM micrographs of live HDF cells loaded with polymersomes encapsulating FITC labelled anti-p65 to facilitate nuclear localization, cells were also stained with the cell permeable nucleic acid stain Syto-9: a) Cells were treated with polymersome-antip65NFκB antibody for 6 h uptake (negative control, unstimulated cells); b) Cells were stimulated with 1 μg/mL of LPS 2 h prior to polymersome-antip65NFκB antibody uptake;

FIG. 11 shows HDF cells treated with polymersomes encapsulating anti-Golgi antibodies: (a) delivery of polymersomes encapsulating the primary antibody followed by delivery of polymersomes encapsulating the secondary antibody into live cells; (b) detail of FIG. 11a; (c) conventional immunolabelling with primary and secondary antibodies; (d) detail of FIG. 11c; and FIG. 12 shows CLSM micrographs of live HDF cells treated with polymersomes encapsulating anti α-tubulin, clearly showing the mitotic spindle.

EXAMPLES

Example 1: Copolymer Synthesis $PMPC_{25}$-$PDPA_{70}$ Synthesis 2-(Methacryloyloxy)ethyl phosphorylcholine (MPC; >99%) was used as received (Biocompatibles UK Ltd). 2-(Diisopropylamino)ethyl methacrylate (DPA) was purchased from Scientific Polymer Products (USA). Copper (I) bromide (CuBr; 99.999%), 2,2'-bipyridine (bpy), methanol and isopropanol were purchased from Aldrich and were used as received. The silica used for removal of the ATRP copper catalyst was column chromatography grade silica gel 60 (0.063-0.200 mm) purchased from E. Merck (Darmstadt, Germany). 2-(N-Morpholino)ethyl 2-bromo-2-methylpropanoate (ME-Br) initiator was synthesized according to a previously reported procedure (Robinson, K. L., et al, *J. Mater. Chem.* 2002, 12, 890).

$PMPC_{25}$-$PDPA_{70}$ copolymer was synthesized by an ATRP procedure, as reported elsewhere (Du, J., et al, *J. Am. Chem. Soc.* 2005, 127, 17982). Briefly, a Schlenk flask with a magnetic stir bar and a rubber septum was charged with Cu (I) Br (25.6 mg, 0.178 mmol) and MPC (1.32 g, 4.46 mmol). ME-Br initiator (50.0 mg, 0.178 mmol) and bpy ligand (55.8 mg, 0.358 mmol) were dissolved in methanol (2 ml), and this solution was deoxygenated by bubbling $N_2$ for 30 minutes before being injected into the flask using a syringe. The [MPC]:[ME-Br]:[CuBr]:[bpy] relative molar ratios were 25:1:1:2. The reaction was carried out under a nitrogen atmosphere at 20° C. After 65 minutes, deoxygenated DPA (6.09 g, 28.6 mmol) and methanol (7 ml) mixture were injected into the flask. After 48 h, the reaction solution was diluted by addition of isopropanol (about 200 ml) and then passed through a silica column to remove the catalyst.

PEO-PDPA Synthesis

The procedure followed Vamvakaki et al in Macromolecules; 1999; 32(6) pp 2088-2090 was adapted as detailed below.

The monohydroxy-capped poly(ethylene oxide) (PEO) was donated by Inspec U. K. GPC analyses gave Mw/Mn's of 1.10 for PEO; degrees of polymerization were either 22 or 45 for PEO. In a typical synthesis, PEO (5.0 g) dissolved in 100 mL of dry THF was added to a round-bottomed flask under dry nitrogen. Potassium naphthalene (2.50 mmol) in THF was added via a double-tipped needle, and the reaction solution was stirred at 30° C. for 1-2 h to form the alcoholate macro-initiator. Freshly distilled tertiary amine methacrylate (5-15 mL) was added, and the polymerization was allowed to proceed for 4 h prior to quenching with methanol. In some cases the polymerizations were conducted at 35 or 50° C. Solvent was removed under vacuum, the copolymer was redissolved in dilute HCl, and the water-insoluble naphthalene was removed by filtration. $PEG_{113}$-$PDPA_{71}$ and $PEG_{10}$-$PDPA_{30}$ were obtained in high yields (95-100%) with good control over copolymer molecular weight.

Example 2: Preparation and Antibody Encapsulation $PMPC_{25}$-$PDPA_{70}$ copolymer (20 mg) was added to a glass vial and dissolved in a solution of 2:1 chloroform:methanol at a concentration of 3 mg/ml. The solvent was evaporated under vacuum, resulting in a copolymeric film deposited on the walls of the vial. The copolymer film was sterilized in an autoclave and then rehydrated under sterile conditions using phosphate buffer saline (100 mM PBS) to form a 0.5% w/w copolymer suspension. The pH of this suspension was dropped to pH 2 to solubilise the film again and the pH was increased to pH 6.0. The Antibody suspension consisting of labelled goat anti-human IgG (unspecific secondary antibodies) was added to the polymer solution. 50 μg of antibody suspension per ml of polymer solution was added. When the cells are to contacted with antibody loaded vesicles, a 1 in 10 dilution of the vesicles in cell medium is used. Thus, the concentration of antibody is 5 μm/ml cell medium, which is around the same as that used in traditional immunolabelling. Vesicles encapsulating the Antibody were purified via gel permeation chromatography (GPC), using a size exclusion column containing Sepharose 4B and using PBS at pH 7.3 to elute the vesicles. The fractions that contained vesicles encapsulating Antibody, as determined by measuring the UV absorption at 260 nm using a Perkin Elmer Lambda 25 UV spectrophotometer, were used to treat the cells in the Examples detailed below.

Example 3: Delivery of Fluorescent Antibodies to Cells

Primary human dermal fibroblasts (HDF) were isolated from skin obtained from abdominoplasty or breast reduction operations (according to local ethically approved guidelines, NHS Trust, Sheffield, UK). Primary cultures of fibroblasts were established as previously described in Ralston et al; Br J. Dermatol. 1999 April; 140(4): 605-15. Briefly, the epidermal layer of the skin was removed by trypsinisation and the remaining dermal layer was washed in PBS. The dermis was then minced using surgical blades and incubated in 0.5% (w/v) collagenase A at 37° C. overnight in a humidified $CO_2$ incubator. A cellular pellet was collected from the digest and cultured in DMEM (Sigma, UK) supplemented with 10% (v/v) foetal calf serum, 2 mM L-glutamine, 100 IU/ml penicillin, 100 mg/ml streptomycin and 0.625 μg/ml amphotericin B. Cells were sub-cultured routinely using 0.02% (w/v) EDTA and used for experimentation between passages 4 and 8.

The cells were seeded $1\times10^5$ cells/well in a 6-well plate (or on coverslips). The next day, the medium was aspirated from the cells and then the $PMPC_{25}\text{-}PDPA_{70}$ polymersomes (1 mg/ml in cell medium) containing first the primary and then the secondary antibody were added directly onto the cells. The procedure followed in Example 2 was used to encapsulate the primary and secondary antibodies into separate populations of vesicles. 5 μg of primary and secondary antibody per ml of medium were loaded on the cell. The cells were incubated at 37° C. for 24 h. The cells were washed three times with PBS. Living cells were directly examined with a confocal microscope (ZEISS LSM 510M).

Figure 1:
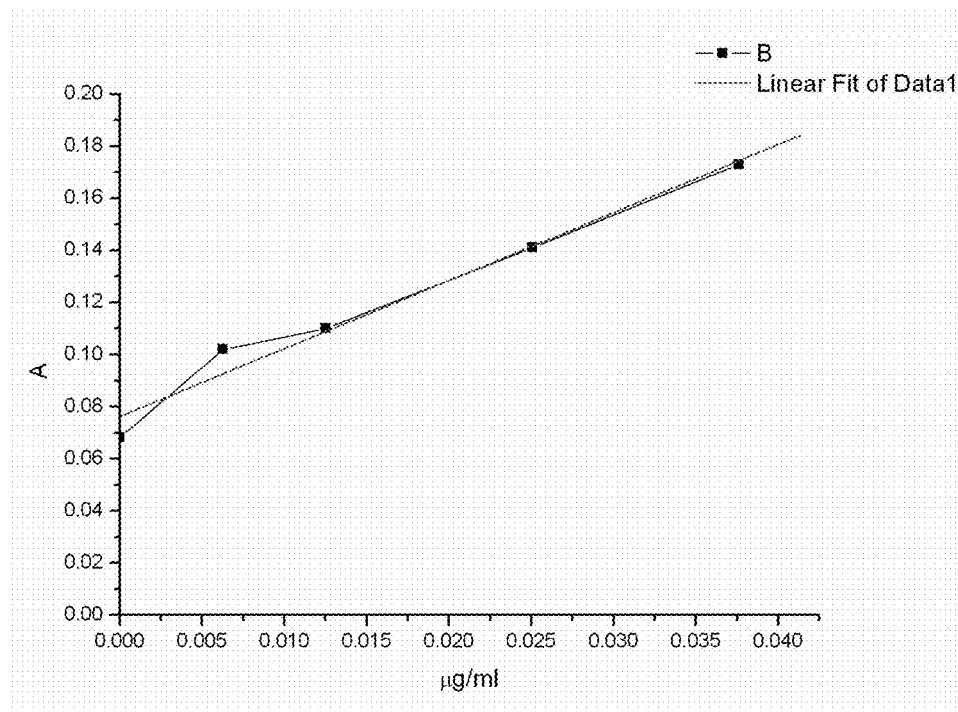
FIG. 1 is a calibration curve of antibody vs absorbance.
Figure 2:
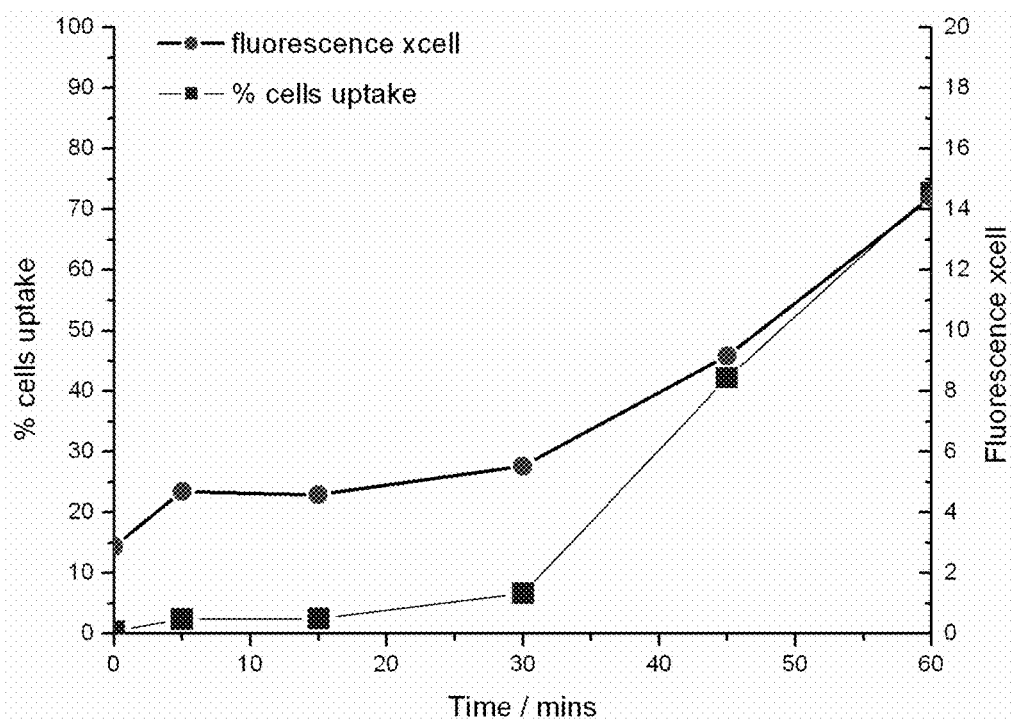
FIG. 2 shows the uptake of fluorescence x cell intensity over time.
Figure 3:
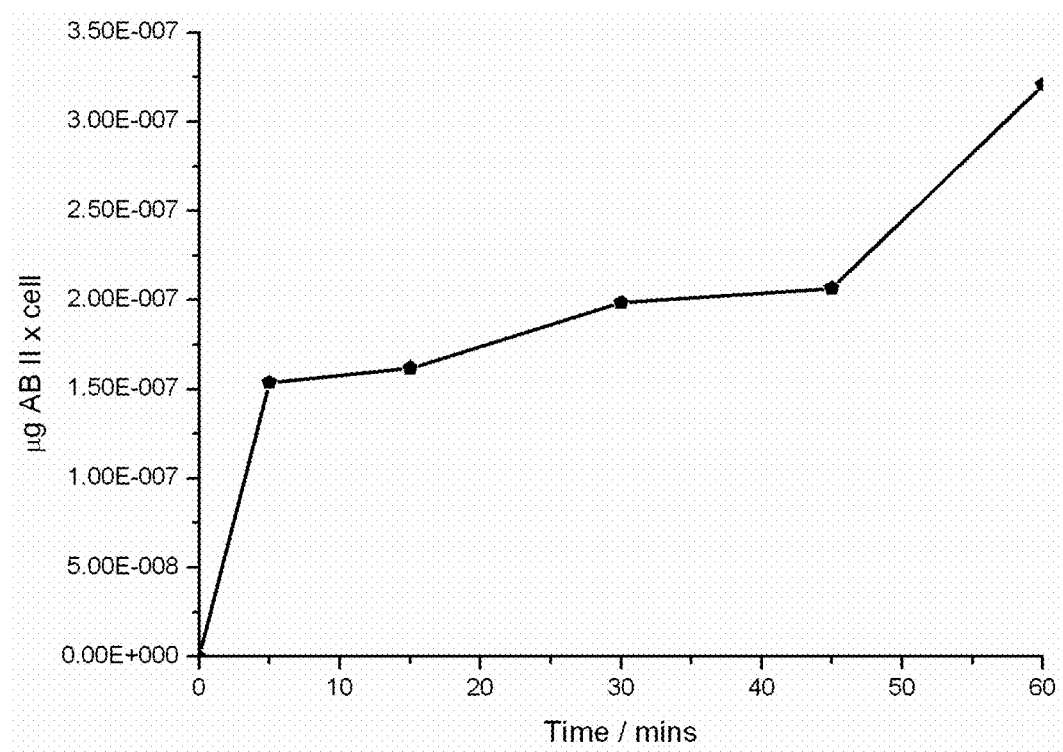
FIG. 3 shows the quantity of antibody taken up by the cells over time.

Quantification of Antibody:

Absorbance of samples was calibrated over a number of different concentrations of secondary antibody (labelled goat anti-human IgG). The calibration curve allowed calculation of the quantity of antibody present in the cell during a kinetic study. Samples of increasing concentration of polymersomes and consequently of secondary antibody were prepared (0.0 μg ml, 0.0063 μg/ml, 0.0013 μg/ml, 0.0251 μg/ml, 0.0376 μg antibody per ml PBS). The main experiment was performed loading the polymersomes (1 mg/ml in normal culture medium) on the top of the cells. Samples were incubated over a number of time points (5, 15, 30, 45, 60 minutes) to obtain data on cellular uptake of vesicles (see FIG. 1). All samples were then washed five times with PBS to remove any unloaded vesicles. Trypsine EDTA was used for two minutes to detach the cells from the wellplate. The cells were then prepared in PBS in order to run the flowcytometric analysis, as detailed in Example 5. The polymersomes were taken up by every cell, with 70% of cell uptake after one hour incubation (FIG. 2). Fluorescence per cell increased sharply after the initial loading of the polymersomes, intensity remained relatively stable from 5-30 min, fluctuating between 22 and 28% cell uptake. After the 30 min time point a linear increase in the fluorescence per cell was observed. 300 μl was taken to evaluate the absorbance and consequently to estimate the quantity of antibody present in each cell. Large quantities of active antibody were delivered inside live cells (FIG. 3).

Example 4: Imaging Using Confocal Laser Scanning (CLS) Microscopy

The efficiency of polymersome delivery was investigated by seeding the cells at $5\times10^4$ cells/well, as previously described and then contacting them with polymersome-encapsulated primary and secondary antibodies. Cells were loaded and imaged using the confocal microscope. The control samples for fixing and staining with the primary (Anti-Golgin-97(human) mouse IgG1 monoclonal CDF4) and secondary antibody ALEXAFLUOR 546 goat Anti-human IgG) were prepared following the immunostaining protocol.

Immunostaining with Primary and Secondary Antibodies:

Cells already grown on coverslips were washed 3× with PBS and fixed with 4% paraformaldehyde. Then the membranes were permeabilised with Triton 0.1% for 20 minutes and unreacted binding sites were blocked with 5% BSA for one hour. After this time the primary antibodies were added into 1% BSA solution (Anti-Golgi-97(human) mouse IgG1 monoclonal CDF4 (Anti Golgi) purchased from Invitrogen Ltd) and the plate was left overnight at 4° C. The day after the cover slips were washed again (three times) very carefully and secondary antibody added (ALEXAFLUOR 546 goat Anti-human IgG). Coverslips were incubated in secondary antibody for 2 hours and then washed carefully. The cells and coverslips were mounted directly onto a hanging drop slide to be visualised.

Figure 4:
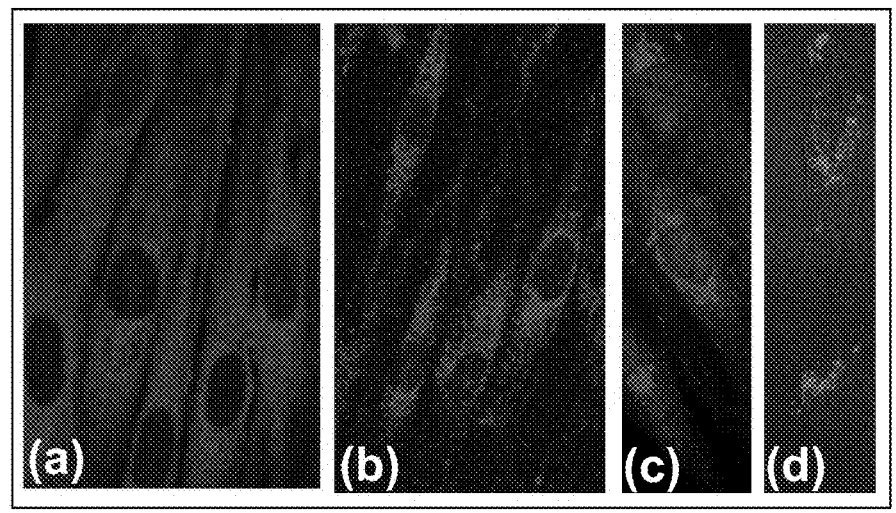
FIG. 4 shows fibroblasts stained with varying treatments: (a) secondary antibody by conventional method; (b) polymersomes containing secondary antibody; (c) primary and secondary antibody by conventional method; (d) with primary antibody encapsulated in polymersomes and secondary antibody encapsulated in polymersomes.

CLS Imaging:

Coverslips were then rinsed with PBS for 3 min. Finally, the coverslips were mounted onto microscope slides and analysed using a CLS microscope. FIG. 4 shows the results of the stained cells and the live cells treated with polymersomes of Examples 1 & 2: Fixed cells with primary and secondary antibody (4c) and secondary antibody-only (4a); and live cells, treated with polymersomes of the invention containing primary and secondary antibody (4d), and secondary antibody-only (4b). To obtain the results in FIG. 4b, live cells were loaded for 24 hours with primary antibodies encapsulated in polymersomes, and then loaded for 2 hours with secondary antibodies encapsulated in polymersomes. Primary antibody is shown to be delivered to an intracellular target (the golgi). It can be seen that the results are almost the same, for both fixed and live cells. The only difference is related to the intensity of the signal because the quantity of antibody available to target the golgi is greater if the cell is treated with triton. Additionally, in fixed cells there is the possibility to wash free-antibody, whereas in live cells, this is not possible because the membrane is completely entact and undamaged. These results demonstrate delivery of active Anti-Golgin antibody within a live cell and specific targeting of the golgi apparatus.

In FIG. 4b, unspecificity of secondary antibody alone in the cells is demonstrated. The results are equivalent to those obtained in FIG. 4a (delivery of secondary antibody with no BSA blocking in traditional immunolabelling). In FIGS. 4c and 4d it can be seen that delivering both primary and secondary antibody within different populations of vesicles makes the binding more specific.

Example 5: Flow Cytometry

Figure 5A:
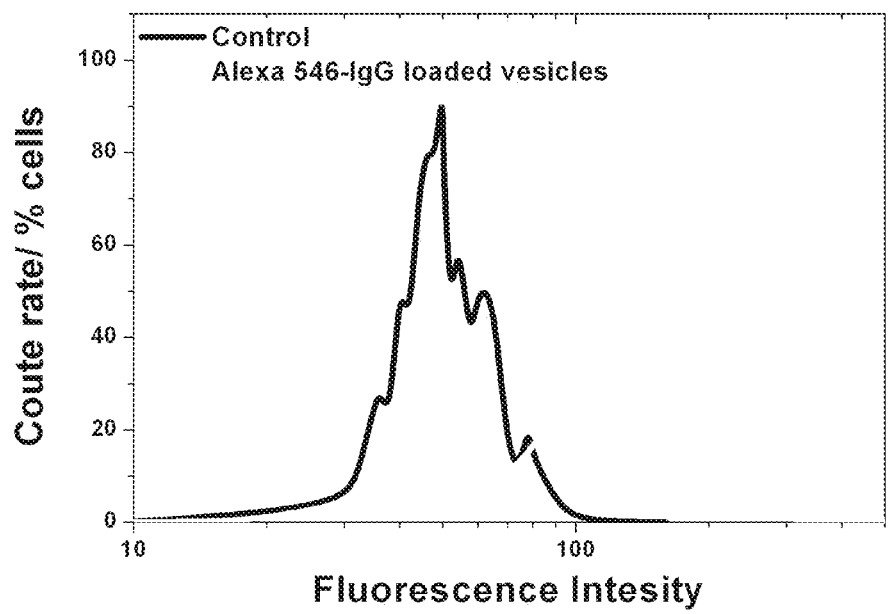
FIG. 5 shows (a) the flow cytometry results and (b) the CLS image of fluorescent secondary antibody uptake in fibroblasts.
Figure 5B:
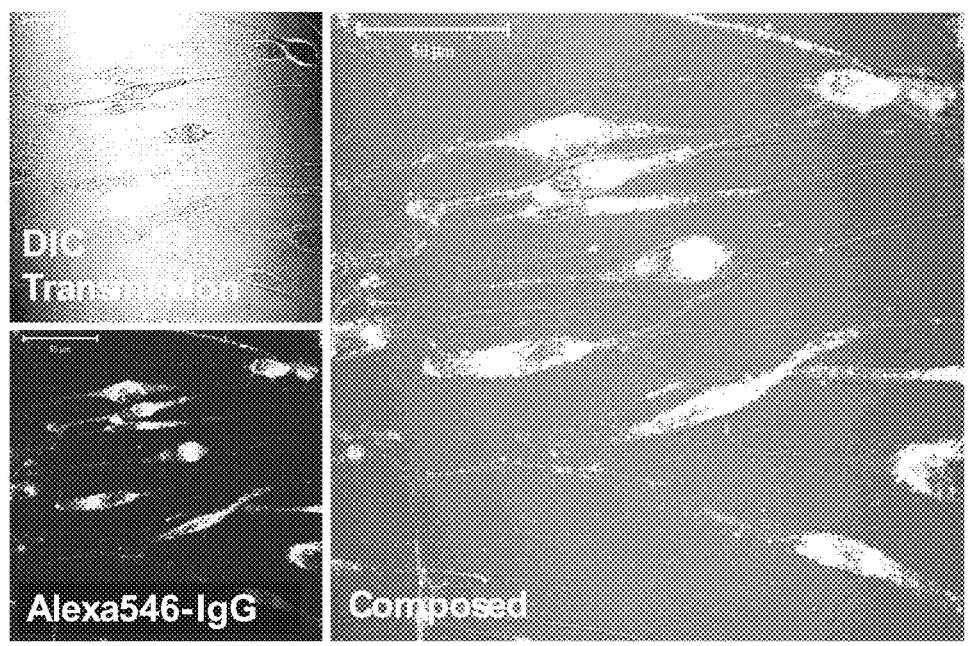
Figure 6:
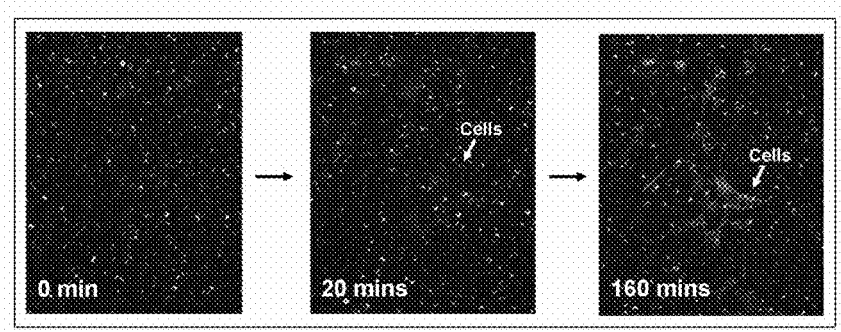
FIG. 6 shows the live uptake by HDFs of polymersomes encapsulating secondary antibodies.

Flow Cytometry is a technique that provides cell counting and viability assay. The first photomultiplier identifies all events with fluorescence centered at 580 nm, the second, all the events with fluorescence centered at 675 nm. The data are then presented as in FIG. 5a, which clearly shows the majority of fibroblasts have taken up the secondary antibody (ALEXAFLUOR 546 goat Anti-human IgG), as demonstrated by the CLS image FIG. 5b.

Example 6

The procedure of Example 2 was used to form polymersomes with encapsulated antibody anti-human actin. The polymersomes were contacted with live human dermal fibroblasts using the method of Example 3. The fibrous structure of the actin was clearly visible. On a colour image, the green actin (colour antibody) and red/yellow auto fluorescence of the cell could clearly be distinguished.

Example 7: Endosomal Escape of Antibodies Delivered Via Polymersomes

Figure 7:
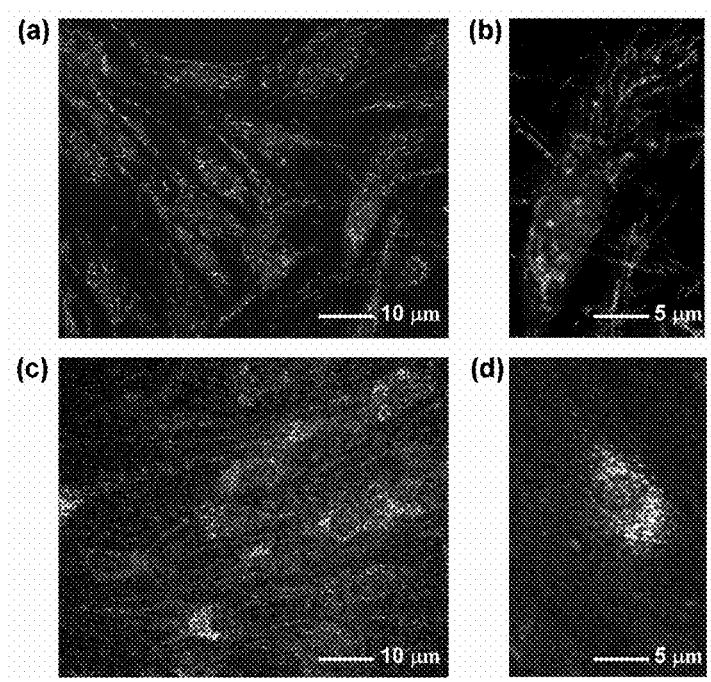
FIG. 7 shows (a) CLSM micrographs of live HDF cells loaded with polymersomes encapsulating primary anti α-tubulin coupled with trypan blue; (b) detail of FIG. 7a; (c) CLSM micrographs of live HDF cells loaded with polymersomes encapsulating primary anti α-tubulin only; (d) detail of FIG. 7c.

FIG. 7 displays three slides taken from a video showing that fluorescence from the visualized cells rises constantly, slowly filling up the cells' cytosol. The most important finding from these studies is that PMPC-PDPA polymersomes are not only taken up by cells but they are also able to deliver material into the cytosol, suggesting that the conventional endocytic pathway can be avoided.

Example 8: Antibody Integrity Post-Intracellular Delivery from Polymersomes

Integrity of antibodies was demonstrated by verifying the targeting ability of primary labelled antibodies by means of CLSM (FIG. 7). In FIGS. 7a and 7b polymersomes loaded with anti α-tubulin FITC labelled primary antibodies have been exposed to live HDF cells for 24 hours. Tubulin filaments have a wide presence within the cell cytosol. Tubulin filaments (white channel) are shown to be clearly marked confirming the target effect, the protection from environmental degradation and homogeneous release within the cell cytosol.

The osmotic shock encountered within the endosome after polymersome internalization does not guarantee 100% of release of the endosome contents. The release mechanism works by equilibration of solute concentration. Thereafter, ~50% of the contents remain entrapped in the endocytic pathway, still conserving its fluorescence. This emission compromises the final image acquisition (FIGS. 7c and 7d) giving high background noise. FIG. 7b shows an improvement in resolution by coupling the labelled antibodies with a black quencher, trypan blue. Antibodies released from endosomes exclusively stain α-tubulin, while trypan-blue quenches the antibodies remaining in the endosomes. The released trypan blue simply diffuses within the cytosol. The resulting image is thereby improved.

All antibodies were able to match their epitope in the tubulin cytoskeleton. As a control the quencher on its own was encapsulated in polymersomes giving a black micrograph (not shown).

Example 9: Intracellular Delivery of NFκB-p65 Antibody Using Polymersomes

Human dermal fibroblasts were cultured in 6 well plates. Rabbit polyclonal to human NFκB-p65 antibody (Abcam) was encapsulated inside PMPC$_{20}$-PDPA$_{75}$ polymersomes. This antibody was chosen on the basis that it targets a region in the C-terminus of the protein away from specific phosphorylation points that are important for the functionality of the NFκB. Cells were incubated with the polymersomes-antip65 for a period of 6 hours to ensure cellular uptake. To activate NFκB translocation, cells were also stimulated with bacterial lipopolysaccharide (LPS, Sigma-Aldrich). Two different types of stimulation were performed as follows: a) Cells were stimulated (2 h) with 1 mg/mL of LPS 6 h after polymersome-antip65NFκB antibody uptake or b) Cells were stimulated with 1 mg/mL of LPS 2 h prior polymersome-antip65NFκB antibody uptake. As an additional negative control to establish cellular background noise in microscopy, cells were treated with empty polymersomes in PBS (results not shown). The results are summarized in FIG. 8.

The anti p65 antibody was successfully encapsulated and delivered without affecting cellular viability or promoting cellular stress. This is demonstrated in FIG. 8c, where cells treated with polymersomes encapsulating the antibody have a predominant localization of NFκB in the cytosol, indicating that the NFκB is inactive. However, upon activation of the pathway (after stimulation with LPS) the NFκB translocates to the nucleus, and hence we can see a clear signal of the antibody in the nuclear region. This was evidence of the biological functionality of the pathway and of the antibody delivered after treatment in live cells (FIGS. 8a and b). This results are similar to those obtained in traditional immunolabeling with fixed cells (FIG. 9).

The targeting of functional antibodies within the cell using polymersomes can also be exploited to modulate important biological processes directly involved in pathologies. Here, the NFκB model is very useful, as inhibiting intracellularly this pathway could be a great advantage in anti-inflammatory therapeutics. Loading the polymersomes with a higher concentration of the antibody we found that NFκB is unable to translocate (FIG. 10b) to the nucleus thus inhibiting the pathway. (Note the inability of the NFκB to translocate to the nucleus and the perinuclear location instead of this transcriptional factor. This is very much in contrast with the homogeneous distribution through the cytosol in unstimulated cells (as in a));)

Example 10: Demonstration of Polymersome-Delivered Antibody Targeting Effect A targeting effect can be shown by encapsulating primary and secondary antibody. The Golgi has been chosen as a model for a organelle targeting. Since the targeted area is limited, in order to have a detectable signal it is necessary to enlarge the binding site. An epitope can be attached to enlarge the labelled area. Unlabelled primary antibody (Anti-Golgin-97(human) mouse IgG1 monoclonal CDF4) was used. The secondary antibody (ALEXAFLUOR 546 goat Anti-human IgG) specifically labelled the primary antibody. Primary and secondary antibody were encapsulated to treat live HDF cells. Loaded samples were compared to fixed samples by means of confocal laser scanning microscopy (CLSM). Micrographs 11a and 11b show live cells where primary antibodies have been encapsulated and delivered for 24 hours within the cell cytosol. Antibodies have been left to reach their epitope placed on the Golgi apparatus. Afterwards fluorescently labelled secondary antibodies have been separately delivered by means of polymersomes and left matching their primary antibodies previously released. FIGS. 11c and 11d display fixed cells stained with the primary and secondary antibodies through normal immunolabelling. This experiment emphasizes the ability of polymersomes to deliver within live cells bioactive molecules without perturbing their stability and specific targeting.

Example 11: Intracellular Antibody Targeting within the Nucleus

Live immunolabelling is essential to monitor cell life without generating artifacts caused by cell fixation. The technique opens a new window on cell investigation showing relevant cell intracellular details, for example, the mitotic spindle revealed in FIG. 12. The mitotic spindle is the cytoskeletal mechanism which pulls apart the chromosomes into the two daughter cells during mitosis. Antibodies which have been delivered within the cell have escaped the endocytic pathway and diffused through the cell cytosol and are still capable of complexing their target in a classical lock-key model even within the nucleus.

The invention claimed is:
1. A composition comprising nanovesicles and encapsulated within the aqueous core of the nanovesicles, an antibody, wherein the nanovesicles comprise an amphiphilic block copolymer having a hydrophilic block formed from 2-methacryloyloxy ethyl phosphorylcholine and a hydrophobic block formed from 2-(diisopropyl)amino ethyl methacrylate, the ratio of the degree of polymerization of the hydrophilic to hydrophobic block is in the range of 1:2.5 to 1:8, the nanovesicles have a diameter in the range of 50 to less than 1,000 nm, and the degree of polymerization of the hydrophilic block is about 20-25 and the degree of polymerization of the hydrophobic block is about 70-75.

2. A composition according to claim 1, wherein one of the blocks comprises pendant groups which have a $pK_a$ in the range 3.0 to 6.9.

3. A composition according to claim 1, wherein the antibody is capable of specific binding to an endogenous intracellular target.

4. A composition according to claim 1, wherein the antibody is IgG antibody.

5. A composition according to claim 1, wherein the antibody is IgG1 antibody.

6. A composition according to claim 1, wherein the antibody is NFκB-p65 antibody.

7. A composition according to claim 1, wherein the composition comprises a primary antibody and a secondary antibody.

8. A composition according to claim 7, wherein the primary antibody is anti-Golgin-97(human) mouse IgG1 monoclonal CDF4 antibody.

9. A composition according to claim 7, wherein the secondary antibody is goat Anti-human IgG antibody having a fluorescent label.

10. A composition according to claim 7, wherein the composition comprises anti-Golgin-97(human) mouse IgG1 monoclonal CDF4 antibody as a primary antibody and goat Anti-human IgG antibody having a fluorescent label as a secondary antibody.

11. A composition according to claim 2, wherein the hydrophobic block comprises pendent groups which have a $pK_a$ in the range of 3.0 to 6.9.

12. A composition according to claim 11, wherein the $pK_a$ is in the range of 4.0 to 6.9.

13. A composition according to claim 2, wherein the $pK_a$ is in the range of 4.0 to 6.9.

14. A method for forming a composition according to claim 1, comprising the steps:
   (i) dispersing the amphiphilic copolymer in an aqueous medium;
   (ii) acidifying the composition formed in step (i);
   (iii) adding the antibody to the acidified composition; and
   (iv) raising the pH to around neutral to encapsulate the antibody.

15. A method according to claim 14, comprising a preliminary step, before step (i), wherein the amphiphilic copolymer is dissolved in an organic solvent in a reaction vessel and the solvent is then evaporated to form a film on the inside of the reaction vessel.

16. An in vitro method of delivering an antibody into a cell comprising contacting a composition according to claim 1 with the cell.

17. A method according to claim 16, wherein the cell is alive.

18. A method according to claim 16, wherein the nanovesicles are taken up by the cell and once inside the cell, the nanovesicles dissociate and release antibody, which binds to an intracellular target.

19. A method of delivering an antibody to a patient in need thereof, comprising administering a composition according to claim 1 to the patient in need thereof.

20. A method according to claim 19, wherein an antibody is delivered into a cell.

* * * * *